United States Patent [19]

Prücher et al.

[11] Patent Number: 5,232,931
[45] Date of Patent: Aug. 3, 1993

[54] OXAZOLIDINONES

[75] Inventors: Helmut Prücher, Heppenheim; Henning Böttcher, Darmstadt; Christoph Seyfried, Jugenheim; Anton Haase, Mühltal; Klaus-Otto Minck, Ober-Ramstadt; Rudolf Gottschlich, Reinheim, all of Fed. Rep. of Germany

[73] Assignee: Merck Patent Gesellschaft mit Beschrankter Haftung, Darmstadt, Fed. Rep. of Germany

[21] Appl. No.: 706,147

[22] Filed: May 28, 1991

[30] Foreign Application Priority Data

May 29, 1990 [DE] Fed. Rep. of Germany ....... 4017211

[51] Int. Cl.[5] ............... A61K 31/445; C07D 498/18; C07D 498/20
[52] U.S. Cl. ..................... 514/321; 514/278; 514/320; 546/15; 546/196; 546/197; 546/209
[58] Field of Search ................ 546/196, 197, 209, 15; 514/320, 321, 278

[56] References Cited

U.S. PATENT DOCUMENTS

| | | | |
|---|---|---|---|
| 4,259,338 | 3/1981 | Durant et al. | 546/196 |
| 4,921,887 | 5/1990 | Matsuo | 546/209 |
| 4,970,217 | 11/1990 | Prucher et al. | 546/209 |
| 5,071,859 | 12/1991 | Knudsen | 546/208 |

FOREIGN PATENT DOCUMENTS 2852945  6/1980  Fed. Rep. of Germany ...... 546/197

OTHER PUBLICATIONS

Welstead et al. "4'(2'aminoethyl) Oxazolidinones with Central Nervous System Depressant and Anti-Inflammatory Activity". J. Med. Chem. vol. 16 No. 10, pp. 1129-1132 (1973).

*Primary Examiner*—C. Warren Ivy
*Assistant Examiner*—Celia Chang
*Attorney, Agent, or Firm*—Millen, White, Zelano & Branigan

[57] ABSTRACT

Novel oxazolidinones of the formula I

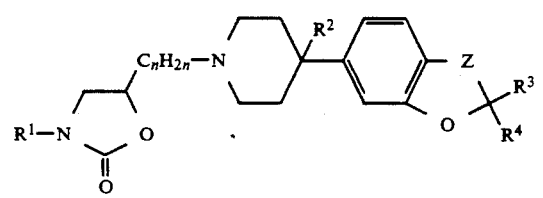

in which $R^1$, $R^2$, $R^3$, $R^4$, Z and n have the meanings defined herein, and their salts have effects on the central nervous system, in particular calming effects.

15 Claims, No Drawings

OXAZOLIDINONES

SUMMARY OF THE INVENTION

The invention relates to new oxazolidinones of the formula I

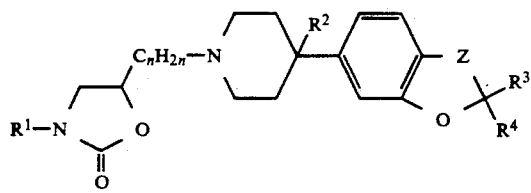

in which $R^1$ is a phenyl radical or mono- or binuclear heteroaryl radical containing 1–4 heteroatoms, each of which is unsubstituted or mono- or disubstituted by A, alkoxy, alkylthio, alkylsulfinyl and/or alkylsulfonyl each having 1–4 C atoms, alkanoyl, alkanoyloxy and/or alkanoylamino each having 1–6 C atoms, F, Cl, Br, CN, OH, $NH_2$, NHA, $NA_2$, $CF_3$ and/or $OCF_3$, $R^2$ is H, CN, OH, $NH_2$, NHA, $NA_2$, $NHCONH_2$, NHCONHA, $NHCONA_2$, alkanoyl, alkanoyloxy or alkanolyamino each having 1–6 C atoms $R^3$ and $R^4$ are each independently H or A or together are alkylene having 4–6 C atoms, A is alkyl with 1–4 C atoms, Z is O, $CH_2$ or O—$CH_2$ and n is 1, 2 or 3, and salts thereof.

An object of the invention is to provide novel compounds which can be used for preparing medicaments.

Upon further study of the specification and appended claims, further objects and advantages of this invention will become apparent to those skilled in the art.

It has been found that the substances mentioned have valuable pharmacological properties in combination with a high tolerance. Thus, they have, for example, a preferably calming (for example sedating, tranquillizing, neuroleptic and/or antidepressant) effect on the central nervous system. Specifically, the compounds have a calming effect on the behavior of mice (for methodics compare Irwin, Psychopharmacologia 13 (1968), 222–257), inhibit the apomorphine-induced climbing behavior in mice (for methodology compare Costall and others, European J. Pharmacol. 50 (1968), 39–50) or induce contra-lateral rotation behavior in Hemiparkinson rats (detectable by the method of Ungerstedt and others, Brain Res. 24 (1970), 485–493) without the occurrence of any significant cataleptic side effects (for methodics compare Dolini-Stola, Pharmakopsychiat. 6 (1973), 189–197). Furthermore, the substances inhibit the binding of tritium-labelled dopamine agonists and dopamine antagonists to striatal receptors (detectable by the method of Schwarcz and others, J. Neurochemistry 34 (1980), 772–778, and Creese and others, European J. Pharmacol. 46 (1977), 377–381) and the binding of tritium-labelled benzomorphans, especially of [$^3$H]-SKF 10,047 to σ-receptors (detectable by the method of Tam, European J. Pharmacol. 109 (1985), 33–41). In addition, the compounds inhibit the linguo-mandibular reflex in the anaesthetised rat (detectable by following the methods of Barnett and others, European J. Pharmacol. 21 (1973), 178–182 and of Ilhan and others, European J. Pharmacol. 33 (1975), 61–64). Furthermore, analgesic and hypotensive actions are observed; thus, in catheterised alert, spontaneously hypertonic rats (strain SHR/NIH-MO//CHB-EMD; for the method compare Weeks and Jones, Proc.Soc.Exptl.Biol.Med. 104 (1960), 646–648), the arterial blood pressure measured directly is lowered after the intragastric application of the compounds.

Compounds of the formula I and their physiologically safe acid addition salts can therefore be used as active substances for medicaments and also as intermediates for preparing other active substances of medicaments.

The invention relates to oxazolidinones of the formula I and their salts.

The invention further relates to a process for preparing oxazolidinones of the formula I and also of salts thereof, characterized in that a compound of the formula II

in which

Ox is the radical

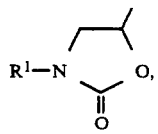

$X^1$ is X or $NH_2$,

X is Cl, Br, I, OH or a reactive functionally modified OH group and $R^1$ and n have the meanings given, is reacted with a compound of the formula III

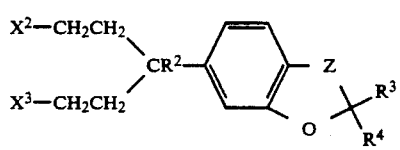

in which $X^2$ and $X^3$ are identical or different and, if $X^1$ is $NH_2$, are each X, otherwise together they are NH and $R^2$, $R^3$, $R^4$ and Z have the meanings given, and/or that a compound which otherwise corresponds to the formula I but contains, instead of one or more hydrogen atoms, one or more reducible groups and/or one or more additional C—C and/or C—N bonds is treated with a reducing agent or that a compound of the formula IV

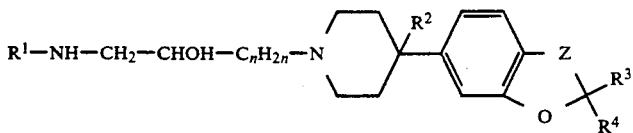

in which $R^1$, $R^2$, $R^3$, $R^4$, Z and n have the meanings given are reacted with a reactive derivative of carbonic acid and/or that, if desired, in a compound of the formula I an O-alkyl group is cleaved to give an OH group and/or a compound of the formula I is converted by reduction to another compound of the formula I, and/or that a base of the formula I is converted to one of its salts by treatment with an acid.

In the radicals $R^1$, $R^2$, $R^3$ and $R^4$, A is preferably methyl, furthermore also ethyl, n-propyl, isopropyl, n-butyl, isobutyl, sec.-butyl or tert.-butyl. Alkoxy is preferably methoxy, furthermore also ethoxy, n-propoxy, isopropoxy, n-butoxy, isobutoxy, sec.-butoxy or tert.-butoxy. Alkylthio is preferably methylthio, furthermore also ethylthio, n-propylthio, isopropylthio, n-butylthio, isobutylthio, sec.-butylthio or tert.-butylthio. Alkylsulfinyl is preferably methylsulfinyl, furthermore also ethylsulfinyl, n-propylsulfinyl, isopropylsulfinyl, n-butylsulfinyl, isobutylsulfinyl, sec.-butylsulfinyl or tert.-butylsulfinyl. Alkylsulfonyl is preferably methylsulfonyl, furthermore also ethylsulfonyl, n-propylsulfonyl, isopropylsulfonyl, n-butylsulfonyl, isobutylsulfonyl, sec.-butylsulfonyl or tert.-butylsulfonyl. Alkanoyl is preferably acetyl or propionyl, furthermore also formyl or butyryl.

Alkanoyloxy is preferably formyloxy or acetoxy, furthermore, for example, also propionyloxy, butyryloxy, isobutyryloxy, pentanoyloxy or hexanoyloxy. Alkanoylamino is preferably formamido or acetamido, furthermore, for example, also propionamido, butyramido, isobutyramido, pentanamido or hexanamido.

In the radical $R^1$, each of the aryl rings of the mono- or binuclear heteroaryl radical has 4-7 ring atoms, 1-3 of which are hetero atoms (N, S, O), there being 1-4 hetero atoms in total, all remaining atoms being C atoms. In a binuclear structure, the two rings can be fused or covalently bonded.

The radical $R^1$ is preferably unsubstituted or monosubstituted phenyl. If $R^1$ is a substituted phenyl group, it can, however, also be disubstituted, it being possible for the substituents to be identical or different. Preferred substituents on the phenyl group are acetyl, methyl, methoxy, F, Cl, CN or $CF_3$; furthermore, preferable substituents are ethyl, ethoxy, Br and/or OH. In detail, $R^1$ is preferably p-methoxyphenyl or p-fluorophenyl, furthermore phenyl, o-, m- or p-tolyl, o-, m- or p-methoxyphenyl, o- or m-fluorophenyl, o-, m- or p-chlorophenyl, o-, m- or p-trifluoromethylphenyl, or o-, m- or p-trifluoromethoxyphenyl, furthermore, o-, m- or p-ethylphenyl, o-, m- or p-ethoxyphenyl o-, m- or p-bromophenyl, o-, m- or p-hydroxyphenyl, o-, m- or p-N,N-dimethylaminophenyl, 2,3-, 2,4-, 2,5-, 2,6-, 3,4- or 3,5-dimethylphenyl, 2,3-, 2,4-, 2,5-, 2,6-, 3,4- or 3,5-dimethoxyphenyl, 2,3-, 2,4-, 2,5-, 2,6-, 3,4- or 3,5-dimethoxyphenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dihydroxyphenyl, 2-methyl-4-chlorophenyl.

The radical $R^1$ can also be a mono- or binuclear heteroaryl radical containing 1-4 heteroatoms, which contains preferably 5 or 6 ring members in each ring. Preferably, the heteroatoms are O, S and/or N. In detail, heteroaryl radicals are preferably 2- or 3-furyl, 2- or 3-thienyl, 2-, 3- or 4-pyridyl, furthermore 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 4-, 5- or 6-pyrimidinyl, furthermore 1,2,3-triazol-1-, -4- or -5-yl, 1,2,4-triazol-1-, -3- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 2,1,5-thiadiazol-3- or -4-yl, 2-, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-indolyl, 1-, 2-, 4-or 5-isoindolyl, 1-, 2-, 4- or 5-benzimidazolyl,1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolyl, 2-, 4-, 5-, 6-, 7- or 8-quinazolyl, 2-, 5- or 6-quinoxalinyl.

The radical $R^2$ is preferably OH, N,N-dimethylamino, N'-methyl-ureido, acetoxy, propionyl, cyano or acetamido. The radicals $R^3$ and $R^4$ are preferably each H or together tetra- or pentamethylene. Z is preferably 0, furthermore also $CH_2$ or $O-CH_2$.

The parameter n is preferably 1 or 2. The group $C_nH_{2n}$ is preferably —$(CH_2)_n$—, i.e., individually it is preferably —$CH_2$—, —$CH_2CH_2$— or —$CH_2CH_2CH_2$—, but also —$CH(CH_3)$—, —$CH(CH_3)CH_2$—, —$CH_2CH(CH_3)$— or —$C(CH_3)_2$.

Accordingly, the invention relates in particular to those compounds of the formula I in which at least one of the radicals mentioned has one of the abovementioned meanings, in particular of the abovementioned preferred meanings. Some preferred groups of compounds correspond to the formula I, in which the radicals and parameters which have not been mentioned individually have the meaning given, but in which (a) $R^1$ is phenyl, tolyl, methoxyphenyl, ethoxyphenyl, fluorophenyl, chlorophenyl, hydroxyphenyl, trifluoromethylphenyl or dimethoxyphenyl;

(b) $R^1$ is phenyl, o-, m- or p-tolyl, m- or p-methoxyphenyl, p-ethoxyphenyl, p-fluorophenyl, p-chlorophenyl, m- or p-hydroxyphenyl, m-trifluoromethylphenyl or 3,4-dimethoxyphenyl;

(c) $R^1$ is p-methoxyphenyl or p-fluorophenyl;

(d) —$C_nH_{2n}$— is —$CH_2$— or —$CH_2CH_2$—;

In detail, all compounds of the abovementioned formulae are preferred in which $R^1$ has one of the abovementioned preferred meanings, in which furthermore the group —$C_nH_{2n}$—, is —$CH_2$— or —$CH_2CH_2$— and/or $R^2$ is OH and/or $R^3$ and/or $R^4$ are H.

As for the preparation of the compounds of the formula I, it is carried out by methods known per se, such as are described in the literature (for example in the standard works such as Houben-Weyl, Methoden der Organischen Chemie (Methods of Organic Chemistry), Georg-Thieme-Verlag, Stuttgart; Organic Reactions, John Wiley & Sons, Inc., New York), under reaction conditions such as are known and suitable for the reactions mentioned. For these reactions, variations known per se which are not mentioned here in detail can also be used.

The starting materials for the process claimed can, if desired, also be formed in situ, such that they are not isolated from the reaction mixture but immediately reacted further to give the compounds of the formula I.

$X^1$ in the compounds of the formula II is preferably X; accordingly, $X^2$ and $X^3$ in the compounds of the formula III are together preferably NH. The radical X is preferably Cl or Br; but it can also be I, OH or a reactive functionally modified OH group, in particular alkylsulfonyloxy having 1-6 C atoms (for example methanesulfonyloxy) or arylsulfonyloxy having 6-10 C atoms (for example, benzenesulfonyloxy, p-toluenesulfonyloxy, 1- or 2-naphthalene-sulfonyloxy).

Accordingly, the compounds of the formula I can be obtained in particular by reaction of compounds of the formulae $Ox—C_nH_{2n}—Cl$, $Ox—C_nH_{2n}—Br$ or $Ox—C_nH_{2n}—OSO_2CH_3$ with compounds of the formula III, in which $X^2$ and $X^3$ together represent an NH group (designated below as IIIa).

Some of the compounds of the formulae II and III are known; the unknown compounds of the formulae II and III can easily be prepared analogously to the known compounds. Primary alcohols of the formula $Ox—C_nH_{2n}—OH$ can be obtained, for example, by reduction of the corresponding carboxylic acids or their esters. Treatment with thionyl chloride, hydrogen bromide, phosphorus tribromide or similar halogen compounds gives the corresponding halides of the formula $Ox—C_nH_{2n}—Hal$. The corresponding sulfonyloxy compounds are obtainable from the alcohols $Ox—C_nH_{2n}—OH$ by reaction with the corresponding sulfonyl chlorides. The iodine compounds of the formula $Ox—C_nH_{2n}—I$ are obtainable, for example, by the action of potassium iodide on the corresponding p-toluenesulfonic esters. The amines of the formula $Ox—C_nH_{2n}—NH_2$ can be prepared, for example, from the halides with potassium phthalimide or by reduction of the corresponding nitriles.

The compounds of the formula IIIa are in part known (compare German Offenlegungsschrift 2,060,816, which corresponds to U.S. Pat. No. 3,821,234) and can be obtained, for example, by reaction of 4-piperidone with 3,4-dialkylenedioxyphenyl-M, benzofuranyl-5-M or benzo-1,4-dioxanyl-6-M (in which M is an Li atom or MgHal), subsequent hydrolysis to give the corresponding 4-hydroxy-4-(3,4-alkylidenedioxyphenyl)-, -4-(5-benzofuranyl)- or -4-(benzo-1,4-dioxan-6-yl)- piperidines and, if desired, subsequent hydrogenation to give 4-(3,4-alkylidenedioxyphenyl)-, -4-(5-benzofuranyl)- or -4-(benzo-1,4-dioxan-6-yl)-piperidines. Compounds of the formula III ($X^2$ and $X^3$ are each X) can be prepared, for example, by reduction of appropriate diesters to give diols of the formula III ($X^2=X^3=OH$) and, if desired, subsequent reaction with $SOCl_2$ or $PBr_3$.

The reaction of compounds II and III is carried out by methods such as are known from the literature for the alkylation of amines. The components can be fused with one another in the absence of a solvent, if necessary in a sealed tube or in an autoclave. However, it is also possible to react the compounds in the presence of an inert solvent. Examples of suitable solvents are hydrocarbons such as benzene, toluene, xylene; ketones such as acetone, butanone; alcohols such as methanol, ethanol, isopropanol, n-butanol; ethers such as tetrahydrofuran (THF) or dioxane; amides such as dimethylformamide (DMF) or N-methylpyrrolidone; nitriles such as acetonitrile; where appropriate even mixtures of these solvents with one another or mixtures with water. It can be advantageous to add an acid-binding agent, for example an alkali or earth alkali metal hydroxide, carbonate or bicarbonate or another salt of a weak acid of the alkali metals or alkaline earth metals, preferably of potassium, sodium or calcium, or to add an organic base such as triethylamine, dimethylaniline, pyridine or quinoline or an excess of the amine component $Ox—C_nH_{2n}—NH_2$ or of the compound of the formula IIIa. Depending on the conditions used, the reaction temperature is approx. 0° and 150°, usually between 20° and 130°.

Furthermore, it is possible to obtain a compound of the formula I by treating a precursor which instead of hydrogen atoms contains one or more reducible group(s) and/or one or more additional C—C and/or C—N bond(s) with a reducing agent, preferably at temperatures between −80° and +250° in the presence of at least one inert solvent.

Reducible groups (replaceable by hydrogen) are, in particular, oxygen in a carbonyl group, hydroxyl, arylsulfonyloxy (for example p-toluenesulfonyloxy), N-benzenesulfonyl, N-benzyl or O-benzyl.

In general, it is possible to convert compounds which have only one or those which have two or more of these groups or additional bonds next to each other to a compound of the formula I by reduction. Preferably, this is done by catalytic hydrogenation, by nascent hydrogen or by certain complex metal hydrides such as $NaBH_4$.

One group of preferred starting materials for the reduction corresponds to the formula VI

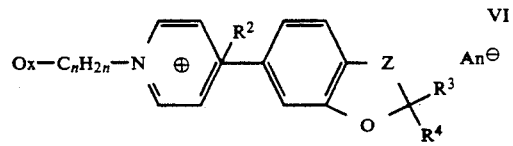

in which Ox, $R^3$, $R^4$, Z and n have the meanings mentioned and $An^\ominus$ is an anion of a strong acid, preferably $Cl^\ominus$ or $Br^\ominus$. Compounds of the formula VI can be prepared, for example, by reaction of a compound of the formula II with a 4-(3,4-alkylidenedioxyphenyl)-pyridine, a 4-(benzo-1,4-dioxan-6-yl)-piperidine or a 4-(2,3-dihydrobenzo-fur-5-yl)piperidine under the conditions given above for the reaction of II and III.

Suitable catalysts for the catalytic hydrogenation are for example noble metal, nickel and cobalt catalysts. The noble metal catalysts can be present on support materials (for example, platinum or palladium on charcoal, palladium on calcium carbonate or strontium carbonate), as oxide catalysts (for example, platinum oxide), or as finely divided metal catalysts. Nickel and cobalt catalysts are preferably used as Raney metals, nickel is also used on kieselguhr or pumice as support material. The hydrogenation can be carried out at room temperature and atmospheric pressure or even at elevated temperature and/or elevated pressure. Preferably, the reaction is carried out at pressures between 1 and 100 atmospheres and at temperatures between −80° and +150°, primarily between room temperature and +100°. The reaction is preferably carried out in an acidic, neutral or basic range and in the presence of a solvent such as water, methanol, ethanol, isopropanol, n-butanol, ethyl acetate, dioxane, acetic acid or THF; mixtures of these solvents with one another can also be used.

If nascent hydrogen is used as the reducing agent, it can be generated, for example, by treating metals with weak acids or with bases. Thus, for example a mixture of zinc with alkali metal hydroxide solution or of iron with acetic acid can be used. The use of sodium or another alkali metal in an alcohol such as ethanol, isopropanol, butanol, amyl or isoamyl alcohol or phenol is also suitable. Furthermore, an aluminium-nickel alloy in an alkaline-aqueous solution, with or without ethanol, can be used. Even amalgamated sodium or aluminium in an aqueous-alcoholic or aqueous solution are suitable for generating nascent hydrogen. The reaction can also be carried out in a heterogeneous phase, in which case an aqueous and a benzene or toluene phase is preferably used.

Reducing agents which can also be used are complex metal hydrides such as $NaBH_4$, diisobutylaluminium hydride or $NaAl(OCH_2CH_2OCH_3)_2H_2$ and also diborane, if desired, with the addition of catalysts such as $BF_3$, $AlCl_3$ or LiBr. Suitable solvents are, in particular, ethers such as diethyl ether, di-n-butyl ether, THF, dioxane, diglyme or 1,2-dimethoxyethane and also hydrocarbons such as benzene. Suitable solvents for a reduction with $NaBH_4$ are primarily alcohols such as methanol or ethanol, furthermore water and also aqueous alcohols. Using these methods, the reduction is preferably carried out at temperatures between $-80°$ and $+150°$, in particular between about 0° and about 100°.

Catalytic hydrogenation of compounds of the formula VI usually gives the corresponding piperidine derivatives.

Compounds of the formula I are also obtainable by reaction of amino alcohols of the formula V with reactive derivatives of carbonic acid. Suitable examples of those are preferably dialkyl carbonates such as dimethyl or diethyl carbonate, esters of chloroformic acid such as methyl or ethyl chloroformate, N,N'-carbonyldiimidazole or phosgene. The reaction is preferably achieved in the presence of an inert solvent, preferably of a halogenated hydrocarbon such as chloroform, of a hydrocarbon such as toluene or of an amide such as DMF at temperatures between about 20° and about 200°, preferably between 100° and 150°. The carbonic acid derivative is preferably used in excess.

Furthermore, a compound of the formula I can, if desired, be converted by methods known per se to another compound of the formula I.

Thus ethers (O-alkyl derivatives) can be cleaved, giving the corresponding hydroxy derivatives. For example, the ethers can be cleaved by treatment with the dimethyl sulfide-boron tribromide complex, for example in toluene, 1,2-dichloroethane, THF or dimethyl sulfoxide, by fusion with pyridinium or anilinium hydrohalides, preferably pyridinium hydrochloride, at about 150°–250°, with HBr/acetic acid or with Al trihalides in chlorinated hydrocarbons such as 1,2-dichloroethane.

The compounds of the formula I can have one or more asymmetric centers. Accordingly, they can be obtained in their preparation as racemates or, if optically active starting materials are used, also in optically active form. If the compounds have two or more asymmetric centers, they are generally formed from the synthesis as mixtures of racemates, from which the individual racemates can be isolated in pure form, for example, by recrystallization from inert solvents. The racemates obtained can, if desired, be resolved into their optical antipodes mechanically or chemically by methods known per se. Preferably, the racemate is reacted with an optically active resolving agent to form diastereomers. Examples of suitable resolving agents are optically active acids, such as the D and L forms of tartaric acid, dibenzoyltartaric acid, diacetyltartaric acid, camphorsulfonic acids, mandelic acid, maleic acid or lactic acid. The various forms of diastereomers can be resolved in a manner known per se, for example by fraction crystallization, and the optically active compounds of the formula I can be liberated from the diastereomers in a manner known per se.

After a base of the formula I has been obtained, it can be converted with an acid to the corresponding acid addition salt. Acids suitable for this reaction are preferably those which give physiologically safe salts. Thus, inorganic acids can be used, for example sulfuric acid, hydrohalic acids, such as hydrochloric acid or hydrobromic acid, phosphoric acids such as orthophosphoric acids, nitric acid, sulfamic acid, furthermore organic acids, for example aromatic or heterocyclic mono-or polybasic carboxylic, sulfonic or sulfuric acids such as formic acid, acetic acid, propionic acid, pivalic acid, diethylacetic acid, malonic acid, succinic acid, pimelic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalene-mono- and -disulfonic acids, and laurylsulfuric acid. Acid addition salts which are not physiologically safe (for example picrates) can be suitable for the isolation and purification of bases of the formula I.

The free bases of the formula I can, if desired, be liberated from their salts by treatment with strong bases such as sodium hydroxide or potassium hydroxide and sodium carbonate or potassium carbonate.

The invention further relates to the use of compounds of the formula I and their physiologically safe salts for preparing pharmaceutical preparations, in particular by non-chemical methods. For this purpose, they can be brought into a suitable dosage form together with at least one carrier or auxiliary and, if desired, in combination with one or more further active substance(s).

The invention further relates to agents, in particular pharmaceutical preparations, containing at least one compound of the formula I and/or one of its physiologically safe salts. These preparations can be used as medicaments in human and veterinary medicine. Examples of carrier materials are organic or inorganic substances which are suitable for the enteral (for example oral), parenteral or topical application and do not react with the novel compounds, for example water, vegetable oils, benzyl alcohols, polyethylene glycols, gelatin, carbohydrates such as lactose or starch, magnesium stearate, talc, and paraffin jelly. Suitable for enteral application are, in particular, tablets, coated pills, capsules, syrups, juices, drops or suppositories, for parenteral application solutions, preferably oily or aqueous solutions, furthermore suspensions, emulsions or implants, and for topical application ointments, creams, plasters or powders. The novel compounds can also be freeze-dried, and the freeze-dried compounds obtained can be used, for example, for preparing injection preparations.

The preparations mentioned can be sterilized and/or contain auxiliaries such as lubricants, preservatives, stabilizers and/or wetting agents, emulsifiers, salts for influencing the osmotic pressure, buffer substances, colorants, flavorings and/or aromas. If desired, they can also contain one or more further active substances, for example one or more vitamins.

The compounds of the formula I and their physiologically safe salts can be used for the therapeutic treatment of the human or animal body and for fighting diseases, in particular schizophrenia and psychoreactive disturbances and psychopathies, depressions, severe chronic pains and diseases which are accompanied by high blood pressure. The compounds can further be used for the treatment of extrapyramidal disturbances.

The substances according to the invention are usually given by analogy with known, commercially available products (thioridazine, haloperidol), preferably in dosage amounts between about 0.2 and 500 mg, in particular between 0.2 and 50 mg per dosage unit. The daily dosage is preferably between about 0.003 and 10 mg/kg of body weight, especially 0.01–0.1 mg/kg of body weight.

The specific dose amount for each individual patient depends, however, on a wide variety of factors, for example on the activity of the specific compound used, on age, body weight, general state of health, sex, on the food, on the date and route of application, on the rate of excretion, medicament combination and seriousness of disease in question for which the therapy is intended. Preference is given to oral application.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight. The entire disclosure of all applications, patents and publications, cited above and below, and of corresponding German application P 40 17 211.2, filed May 29, 1990, are hereby incorporated by reference.

EXAMPLES

In the following examples, "usual workup" means: if necessary, water is added, the product is extracted with dichloromethane, and separated off, the organic phase is dried over sodium sulfate, filtered, evaporated, and the residue is purified by chromatography over silica gel and/or by crystallization. Temperatures are given in ° C. $[\alpha]=[\alpha]_D^{20}$, c=1 in dimethyl sulfoxide.

EXAMPLE 1

4.10 g of 5-(2-methanesulfonyloxyethyl)-3-p-methoxyphenyloxazolidin-2-one [m.p. 61°–64°; obtainable by reaction of 3,4-epoxy-1-butanol with N-benzyl-p-methoxyaniline to give 1-(N-benzyl-p-methoxyanilino)-butane-2,4-diol (resin), hydrogenolysis to give 1-p-methoxyanilinobutane-2,4-diol (resin), reaction with diethyl carbonate to give 5-(2-hydroxyethyl)-3-p-methoxyphenyloxazolidin-2-one (m.p. 77°–78°) and reaction with $CH_3SO_2Cl$] are boiled together with 3.13 g of 4-hydroxy-4-(3,4-methylenedioxyphenyl)piperidine ("M"), 2.16 g of potassium iodide and 1.8 g of potassium carbonate in 100 ml of acetonitrile for 16 hours, the mixture is cooled, worked up as usual, to give 5-[2-(4-hydroxy-4-(3,4-methylenedioxyphenyl)piperidino)ethyl]-3-p-methoxyphenyloxazolidin-2-one, m.p. 128°–130°.

EXAMPLE 2

Analogously to Example 1, S-(-)-5-[4-hydroxy-4-4-(3,4-methylenedioxyphenyl)piperidinomethyl]-3-p-methoxyphenyloxazolidin-2-one, m.p. 161°; $[\alpha]$ −25.6°, hydrochloride, m.p. 214°–215°; $[\alpha]$ −34.4° is obtained from 4.5 g of R-(−)-5-methanesulfonyloxymethyl-3-p-methoxyphenyloxazolidin-2-one, 3.7 g of "M" hydrochloride, 4.6 g of potassium carbonate and 0.3 g of potassium iodide in 120 ml of acetonitrile by boiling for 20 hours.

The following are obtained analogously from the corresponding 5-hydroxymethyl- and 5-(2-hydroxyethyl)-3-$R^1$-oxazolidin-2-ones:

3-p-fluorophenyl-5-hydroxymethyloxazolidin-2-one
3-p-chlorophenyl-5-hydroxymethyloxazolidin-2-one
3-m-trifluoromethylphenyl-5-hydroxymethyloxazolidin-2-one
3-(3,4-dimethoxyphenyl)-5-hydroxymethyloxazolidin-2-one
3-p-fluorophenyl-5-(2-hydroxyethyl)oxazolidin-2-one
3-p-chlorophenyl-5-(2-hydroxyethyl)oxazolidin-2-one
3-m-trifluoromethylphenyl-5-(2-hydroxyethyl)oxazolidin-2-one
3-(3,4-dimethoxyphenyl)-5-(2-hydroxyethyl)oxazolidin-2-one via the corresponding 5-methanesulfonyloxymethyl-, 5-chloromethyl-, 5-bromomethyl-, 5-(2-methanesulfonyloxyethyl)-, 5-(2-chloroethyl)- or 5-(2-bromoethyl)-3-$R^1$-oxazolidin-2-ones or the formula II, for example:

3-p-fluorophenyl-5-methanesulfonyloxymethyloxazolidin-2-one
3-p-chlorophenyl-5-methanesulfonyloxymethyloxazolidin-2-one
3-m-trifluoromethylphenyl-5-methanesulfonyloxymethyloxazolidin-2-one
3-(3,4-dimethoxyphenyl)-5-methanesulfonyloxymethyloxazolidin-2-one
3-p-methoxyphenyl-5-(2-chloroethyl)oxazolidin-2-one
3-p-fluorophenyl-5-(2-methanesulfonyloxyethyl)oxazolidin-2-one
3-p-chlorophenyl-5-(2-methanesulfonyloxyethyl)oxazolidin-2-one
3-m-trifluoromethylphenyl-5-(2-methanesulfonyloxyethyl)-oxazolidin-2-one
3-(3,4-dimethoxyphenyl)-5-(2-methanesulfonyloxyethyl)oxazolidin-2-one using "M" or "M hydrochloride":
5-[4-hydroxy-4-(3,4-methylenedioxyphenyl)piperidinomethyl]-3-phenyloxazolidin-2-one
5-[4-hydroxy-4-(3,4-methylenedioxyphenyl)piperidinomethyl]-3-m-tolyloxazolidin-2-one
5-[4-hydroxy-4-(3,4-methylenedioxyphenyl)piperidinomethyl]-3-o-methoxyphenyloxazolidin-2-one
5-[4-hydroxy-4-(3,4-methylenedioxyphenyl)-piperidinomethyl]-3-m-methoxyphenyloxazolidin-2-one
5-[4-hydroxy-4-(3,4-methylenedioxyphenyl)-piperidinomethyl]-3-p-methoxyphenyloxazolidin-2-one, RS form,
m.p. 160°–162°

3-p-fluorophenyl-5-[4-hydroxy-4-(3,4-methylenedioxyphenyl)piperidinomethyl]oxazolidin-2-one, S form, m.p. 172°–173°; [α] −23.4°

3-p-chlorophenyl-5-[4-hydroxy-4-(3,4-methylenedioxyphenyl)piperidinomethyl]oxazolidin-2-one, S form, m.p. 163°–165°; [α] −28.6°

5-[4-hydroxy-(3,4-methylenedioxyphenyl)piperidinomethyl]-3-m-trifluoromethylphenyloxazolidin-2-one 3-(3,4-dimethoxyphenyl)-5-[4-hydroxy-4-(3,4-methylenedioxyphenyl)piperidinomethyl]oxazolidin-2-one 3-p-ethoxyphenyl-5-[4-hydroxy-4-(3,4-methylenedioxyphenyl)piperidinomethyl]oxazolidin-2-one, S form, m.p. 139°–141°

5-[2-(4-hydroxy-4-(3,4-methylenedioxyphenyl)piperidino)ethyl]-3-phenyloxazolidin-2-one 5-[2-(4-hydroxy-4-(3,4-methylenedioxyphenyl)piperidino)ethyl]-3-m-tolyloxazolidin-2-one 5-[2-(4-hydroxy-4-(3,4-methylenedioxyphenyl)piperidino)ethyl]-3-o-methoxyphenyloxazolidino-2-one 5-[2-(4-hydroxy-4-(3,4-methylenedioxyphenyl)piperidino)ethyl]-3-m-methoxyphenyloxazolidin-2-one 3-p-fluorophenyl-5-[2-(4-hydroxy-4-(3,4-methylenedioxyphenyl)piperidino)-ethyl]oxazolidin-2-one, RS form, m.p. 143°–145°

3-p-chlorophenyl-5-[2-(4-hydroxy-4-(3,4-methylenedioxyphenyl)piperidino)ethyl]oxazolidin-2-one 5-[2-(4-hydroxy-4-(3,4-methylenedioxyphenyl)piperidino)ethyl]3-m-trifluoromethylphenyloxazolidin-2-one 3-(3,4-dimethoxyphenyl)-4-[4-hydroxy-4-(3,4-methylenedioxyphenyl)piperidino)ethyl]oxazolidin-2-one 3-p-ethoxyphenyl-5-[4-hydroxy-4-(3,4-methylenedioxyphenyl)piperidino)ethyl]oxazolidino-2one.

The following are obtained analogously using 4-(3,4-methylenedioxyphenyl)piperidine:

5-[4-(3,4-methylenedioxyphenyl)piperidinomethyl]-3-phenyloxazolidin-2-one

5-[4-(3,4-methylenedioxyphenyl)piperidinomethyl]-3-o-tolyloxazolidin-2-one 3-o-methoxyphenyl-5-[4-(3,4-methylenedioxyphenyl)piperidinomethyl]oxazolidin-2-one 3-m-methoxyphenyl-5-[4-(3,4-methylenedioxyphenyl)piperidinomethyl]oxazolidin-2-one 3-p-methoxyphenyl-5-[4-(3,4-methylenedioxyphenyl)piperidinomethyl]oxazolidin-2-one, S form, hydrochloride, m.p. 248°–255° (dec.); [α] −34.0°

3-p-fluorophenyl-5-[4-(3,4-methylenedioxyphenyl)piperidinomethyl]oxazolidin-2-one 3-p-chlorophenyl-5-[4-(3,4-methylenedioxyphenyl)piperidinomethyl]oxazolidin-2-one 5-[4-(3,4-methylenedioxyphenyl)piperidinomethyl]-3-trifluoromethylphenyloxazolidin-2-one 3-(3,4-dimethoxyphenyl)-5-[4-(3,4-methylenedioxyphenyl)piperidinomethyl]oxazolidin-2-one 3-p-ethoxyphenyl-5-[4-(3,4-methylenedioxyphenyl)piperdinomethyl]oxazolidin-2-one 5-[2-(4-(3,4-methylenedioxyphenyl)piperidino)ethyl]-3-phenyloxazolidin-2-one 5-[2-(4-(3,4-methylenedioxyphenyl)piperidino)ethyl]-3-o-tolyloxazolidin-2-one 3-o-methoxyphenyl-5-[2-(4-(3,4-methylenedioxyphenyl)piperidino)ethyl]oxazolidin-2-one 3-m-methoxyphenyl-5-[2-(4-(3,4-methylenedioxyphenyl)piperidino)ethyl]oxazolidin-2-one 3-p-methoxyphenyl-5-[2-(4-(3,4-methylenedioxyphenyl)piperidino)ethyl]oxazolidin-2-one 3-p-fluorophenyl-5-[2-(4-(3,4-methylenedioxyphenyl)piperidino)ethyl]oxazolidin-2-one 3-p-chlorophenyl-5-[2-(4-(3,4-methylenedioxyphenyl)piperidino)ethyl]oxazolidin-2-one 5-[2-(4-(3,4-methylenedioxyphenyl)piperidino)ethyl]-3-trifluoromethylphenyloxazolidin-2-one 3-(3,4-dimethoxyphenyl)-5-[2-(4-(3,4-methylenedioxyphenyl)piperidino)ethyl]oxazolidin-2-one 3-p-ethoxyphenyl-5-[2-(4-(3,4-methylenedioxyphenyl)piperidino)ethyl]oxazolidin-2-one.

5-[4-Hydroxy-4-(3,4-isopropylidenedioxyphenyl)piperidinomethyl]-3-p-methoxyphenyloxazolidin-2-one, S form, m.p. 122°–123°; [α] −26.8° is obtained analogously using 4-hydroxy-4-(3,4-isopropylidenedioxyphenyl)piperidine (obtainable by reaction of 1-benzyl-4-piperidinone with 3,4-isopropylidenedioxyphenylmagnesium bromide, subsequent hydrolysis and elimination of the benzyl group).

EXAMPLE 3

A mixture of 1.92 g of 5-aminomethyl-3-phenyloxazolidin-2-one [obtainable by reaction of 5-chloromethyl-3-phenyloxazolidin-2-one with potassium phthalimide and subsequent hydrolysis] and 2.63 g of 1,5-dichloro-3-(3,4-methylenedioxyphenyl)pentane in 40 ml of acetone and 40 ml of water is boiled for 24 hours and worked up as usual, giving 3-phenyl-5-[4-(3,4-methylenedioxyphenyl)piperidinomethyl]oxazolidin-2-one.

EXAMPLE 4

A solution of 4.87 g of 1-(3-p-methoxyphenyloxazolidin-2-one-5-yl-methyl)-4-(3,4-methylenedioxyphenyl)pyridinium bromide [obtainable from 3-p-methoxyphenyl-5-bromomethyloxazolidin-2-one and 4-(3,4-methylenedioxyphenyl)pyridine] in 60 ml of acetic acid is hydrogenated over 1 g of 10% strength Pd/carbon at 20° and atmospheric pressure until the absorption of hydrogen has ceased. After filtration, evaporation and usual workup, 3-p-methoxyphenyl-5-[4-(3,4-methylenedioxyphenyl)piperidinomethyl]oxazolidin-2-one is obtained.

EXAMPLE 5

A mixture of 4.1 g of 4-hydroxy-1-(3-hydroxy-4-p-methoxyanilinobutyl)-4-(3,4-methylenedioxyphenyl)piperidine (obtainable by reaction of p-methoxyaniline with ethyl 3,4-epoxybutyrate to give ethyl 3-hydroxy-4-p-methoxyanilinobutyrate, reduction with LiAlH₄ to 4-p-methoxyanilino-1,3-propanediol, dehydration to the epoxide and reaction with 4-hydroxy-4-(3,4-methylenedioxyphenyl)piperidine), 1.5 g of diethyl carbonate, 0.1 g of sodium and 50 ml of DMF is heated at 120° for 4 hours. Evaporation and usual workup gives 5-[2-(4-hydroxy-4-(3,4-methylenedioxyphenyl)piperidino)ethyl]-3-p-methoxyphenyloxazolidin-2-one.

EXAMPLE 6

A mixture of 10 g of 3-p-methoxyphenyl-5-[4-(3,4-methylenedioxyphenyl)piperidinomethyl]oxazolidin-2-one and 10 g of pyridine hydrochloride is stirred at 160° for 3 hours. Usual workup gives 3-p-hydroxyphenyl-5-[4-(3,4-methylenedioxyphenyl)piperidinomethyl]oxazolidin-2-one.

EXAMPLE 7

A suspension of 3.8 g of 5-[4-hydroxy-4-(3,4-methylenedioxyphenyl)piperidinomethyl]-3-p-methoxyphenyloxazolidin-2-one in 50 ml of 1,2-dichloroethane is added dropwise to a boiling solution of 15.6 g of dimethyl sulphide/boron tribromide complex in 50 ml of 1,2-dichloroethane, the mixture is boiled for another 30 minutes, worked up as usual, to give 5-[4-hydroxy-4-(3,4-methylenedioxyphenyl)piperidinomethyl]-3-p-hydroxyphenyloxazolidin-2-one.

EXAMPLE 8

Analogously to Example 1, there is obtained from 4.5 g of 5-methanesulfonyloxymethyl-3-p-methoxyphenyloxazolidin-2-one, 3.9 g of 4-N,N-dimethylamino-4-(3,4-methylenedioxyphenyl)-piperidine, 1.8 g of potassium carbonate and 2.1 g of potassium iodide in 100 ml of acetonitrile by 20 hours refluxing 3-p-methoxyphenyl-5-[4-N,N-dimethylamino-4-(3,4-methylenedioxyphenyl)-piperidino-methyl]-oxazolidin-2-one, m.p. 130°–132°.

Analogously, there is obtained by reaction of 5-methanesulfonyloxymethyl-3-p-methoxyphenyl-oxazolidin-2-one
with 4-N'-methyl-ureido-4-(3,4-methylenedioxyphenyl)-piperidine:
3-p-methoxyphenyl-5-[4-N'-methyl-ureido-4-(3,4-methylenedioxyphenyl)-piperidino-methyl]-oxazolidin-2-one, m.p. 225°–227° (dec.);
with 4-acetoxy-4-(3,4-methylenedioxyphenyl)-piperidine: 3-p-methoxyphenyl-5-[4-acetoxy-4-(3,4-methylenedioxyphenyl)piperidino-methyl]-oxazolidin-2-one, hydrochloride, m.p. 164°–165°;
with 4-acetamido-4-(3,4-methylenedioxyphenyl)-piperidine:
3-p-methoxyphenyl-5-[4-acetamido-4-(3,4-methylenedioxyphenyl)-piperidino-methyl]-oxazolidin-2-one;
with 4-hydroxy-4-(2,3-dihydro-5-benzofuryl)-piperidine:
3-p-methoxyphenyl-5-[4-hydroxy-4-(2,3-dihydro-5-benzofuryl)piperidino-methyl]-oxazolidin-2-one, m.p. 147°–148°;
with 4-hydroxy-4-benzo-1,4-dioxan-6-yl-piperidine:
3-p-methoxyphenyl-5-[4-hydroxy-4-(benzo-1,4-dioxan-6-yl)-piperidino-methyl-oxazolidin-2-one, hydrochloride,
m.p. 210°–211° (dec.);
with 4-propionyl-4-(3,4-methylenedioxyphenyl)-piperidine: 3-p-methoxyphenyl-5-[4-propionyl-4-(3,4-methylenedioxyphenyl)-piperidino-methyl]-oxazolidin-2-one, m.p. 134°–135°;
with 4-cyano-4-(3,4-methylenedioxyphenyl)-piperidine:
3-p-methoxyphenyl-5-[4-cyano-4-(3,4-methylenedioxyphenyl)-piperidino-methyl]-oxazolidin-2-one, m.p. 135°–137°, hydrochloride, m.p. 264°–266°;
with 4-hydroxy-4-(2,2-pentamethylene-1,3-benzodioxol-5-yl)piperidine:
3-p-methoxyphenyl-5-[4-hydroxy-4-(2,2-pentamethylene-1,3-benzodioxol-5-yl)-piperidino-methyl]-oxazolidin-2-one,
m.p. 157°–159°.

EXAMPLE 9

Analogously to Example 1, there is obtained by reaction of 3.1 g of 4-hydroxy-4-(3,4-methylenedioxyphenyl)-piperidine, with 3.5 g of 5-methanesulfonyloxymethyl-3-p-cyanophenyl-oxazolidin-2-one in presence of 1.4 g of potassium carbonate and 1.5 g of potassium iodide in 100 ml of acetonitrile by 22 hrs. refluxing 3-p-cyanophenyl-5-[4-hydroxy-4-(3,4-methylenedioxyphenyl)-piperidino-methyl]-oxazolidin-2-one.

Analogously, there is obtained by reaction of 4-hydroxy-4-(3,4-methylenedioxyphenyl)-piperidine
with 5-methanesulfonyloxymethyl-3-p-acetylphenyl-oxazolidin-2-one:
3-p-acetylphenyl-5-[4-hydroxy-4-(3,4-methylenedioxyphenyl)piperidino-methyl]-oxazolidin-2-one, m.p. 193°–195°;
with 5-methanesulfonyloxymethyl-3-p-N,N-dimethylaminophenyloxazolidin-2-one:
3-p-N,N-dimethylaminophenyl-5-[4-hydroxy-4-(3,4-methylenedioxyhenyl)-piperidino-methyl]-oxazolidin-2-one;
with 5-methanesulfonyloxymethyl-3-p-trifluoromethoxyphenyloxazolidin-2-one:
3-p-trifluoromethoxyphenyl-5-[4-hydroxy-4-(3,4-methylenedioxyphenyl)-piperidino-methyl]-oxazolidin-2-one;
with 5-methanesulfonyloxymethyl-3-p-N,N-diethylaminophenyloxazolidin-2-one:
3-p-N,N-diethylaminophenyl-5-[4-hydroxy-4-(3,4-methylenedioxyphenyl)-piperidino-methyl]-oxazolidin-2-one;
with 5-methanesulfonyloxymethyl-3-o-cyanophenyl-oxazolidin-2-one:
3-o-cyanophenyl-5-[4-hydroxy-4-(3,4-methylenedioxyphenyl)-piperidino-methyl]-oxazolidin-2-one;
with 5-methansulfonyloxymethyl-3-m-N,N-dimethylaminophenyloxazolidin-2-one:
3-m-N,N-dimethylaminophenyl-5-[4-hydroxy-4-(3,4-methylenedioxyphenyl)-piperidino-methyl]-oxazolidin-2-one.

The following examples relate to pharmaceutical preparations which contain amines of the formula I or their acid addition salts:

EXAMPLE A

Tablets

A mixture of 1 kg of 5-[2-(4-hydroxy-4-(3,4-methylenedioxyphenyl)piperidino)ethyl]-3-p-methoxyphenyloxazolidin-2-one, 4 kg of lactose, 1.2 kg of potato starch, 0.2 kg of talc and 0.1 kg of magnesium stearate is compressed into tablets in a conventional manner and in such a way that each tablet contains 10 mg of active substance.

EXAMPLE B

Coated pills

Analogously to Example A, tablets are pressed and then coated in a conventional manner with a coating consisting of saccharose, potato starch, talc, tragacanth and colorant.

EXAMPLE C

Capsules 2 kg of 5-(-)-5-[4-hydroxy-4-(3,4-methylenedioxyphenyl)piperidinomethyl]-3-p-methoxyphenyloxazolidin-2-one are filled in a conventional manner into hardened gelatin capsules so that each capsule contains 20 mg of active substance.

EXAMPLE D

Ampoules

A solution of (S)-(-)-3-p-fluorophenyl-5-[4-hydroxy-4-(3,4-methylenedioxyphenyl)piperdinomethyl]oxazolidin-2-one hydrochloride in 60 l of twice-distilled water is filtered under sterile conditions, filled into ampoules, freeze-dried under sterile conditions and sealed under sterile conditions. Each ampoule contains 10 mg of active substance.

Analogously tablets, coated pills, capsules and ampoules are obtainable which contain one or more of the remaining active substances of the formula I and/or their physiologically safe acid addition salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An oxazolidinone compound of the formula I

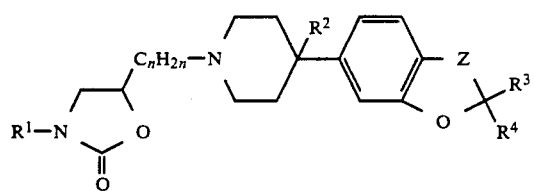

wherein
  $R^1$ is a phenyl radical which is unsubstituted or mono- or disubstituted by $C_{1-4}$-alkyl, $C_{1-4}$-alkoxy, $C_{1-4}$-alkylthio, $C_{1-4}$-alkylsulfinyl, $C_{1-4}$-alkylsulfonyl, $C_{1-6}$-alkanoyl, $C_{1-6}$-alkanoyloxy, $C_{1-6}$-alkanoylamino, F, Cl, Br, CN, OH, $NH_2$, NHA, $NA_2$, $CF_3$ and/or $OCF_3$;
  $R^2$ is H, CN, OH, $NH_2$, NHA, $NA_2$, $NHCONH_2$, NHCONHA, $NHCONA_2$, $C_{1-6}$-alkanoyl, $C_{1-6}$-alkanoyloxy or $C_{1-6}$-alkanoylamino;
  $R^3$ and $R^4$ are each independently H or A, or together are alkylene having 4–6 C atoms;
  A is alkyl with 1–4 C atoms;
  Z is O, $CH_2$ or O—$CH_2$; and
  n is 1, 2 or 3;
  or a physiologically acceptable salt thereof.

2. A compound according to claim 1, wherein said compound is:

a) 5-[4-hydroxy-4-(3,4-methylenedioxyphenyl)-piperidinomethyl]-3-p-methoxyphenyloxazolidin-2-one or a physiologically acceptable salt thereof;
  b) S-(-)-5-[4-hydroxy-4-(3,4-methylenedioxyphenyl)-piperidinomethyl]-3-p-methoxyphenyloxazolidin-2-one or a physiologically acceptable salt thereof;
  c) 5-[2-(4-hydroxy-4-(3,4-methylenedioxyphenyl)-piperidino)ethyl]-3-p-methoxyphenyloxazolidin-2-one or a physiologically acceptable salt thereof;
  d) S-(-)-3-p-fluorophenyl-5-[4-hydroxy-4-(3,4-methylenedioxyphenyl)piperidinomethyl]-oxazolidin-2-one or a physiologically acceptable salt thereof;
  e) 3-p-methoxyphenyl-5-[4-N'-methyl-ureido-4-(3,4-methylenedioxyphenyl)-piperidinomethyl]oxazolidin-2-one or a physiologically acceptable salt thereof; or
  f) 3-p-methoxyphenyl-5-[4-acetamido-4-(3,4-methylenedioxyphenyl)-piperidinomethyl]oxazolidin-2-one or a physiologically acceptable salt thereof.

3. A compound according to claim 1, wherein $R^2$ is OH, N,N-dimethylamino, N'-methyl-ureido, acetoxy, propionyl, cyano or acetamido.

4. A compound according to claim 1, wherein $R^3$ and $R^4$ are each H or together are tetramethylene or pentamethylene.

5. A compound according to claim 1, wherein n is 1 or 2.

6. A compound according to claim 1, wherein $-C_nH_{2n}-$ is $-CH_2-$, $-CH_2CH_2-$ or $-CH_2CH_2CH_2-$.

7. A compound according to claim 1, wherein $R^1$ is phenyl, tolyl, methoxyphenyl, ethoxyphenyl, fluorophenyl, chlorophenyl, hydroxyphenyl, trifluoromethylphenyl or dimethoxyphenyl.

8. A compound according to claim 1, wherein $R^1$ is phenyl, o-, m- or p-tolyl, m- or p-methoxyphenyl, p-ethoxyphenyl, p-fluorophenyl, p-chlorophenyl, m- or p-hydroxyphenyl, m-tri-fluoromethylphenyl or 3,4-dimethoxyphenyl.

9. A compound according to claim 1, wherein $R^1$ is p-methoxyphenyl or p-fluorophenyl.

10. A compound according to claim 1, wherein $-C_nH_{2n}-$ is $-CH_2-$ or $-CH_2CH_2-$.

11. A compound according to claim 1, wherein $R^2$ is OH.

12. A compound according to claim 1, wherein at least one of $R^3$ and $R^4$ is H.

13. A pharmaceutical composition comprising a compound according to claim 1 and a physiologically acceptable carrier.

14. A composition according to claim 13, wherein said composition contains said compound in an amount of about 0.2–500 mg.

15. A composition according to claim 13, wherein said composition contains said compound in an amount of 0.2–50 mg.

* * * * *